(12) United States Patent
Thierfelder et al.

(10) Patent No.: US 9,987,113 B2
(45) Date of Patent: *Jun. 5, 2018

(54) IMPLANTABLE ARTICLE AND METHOD

(71) Applicant: Astora Women's Health, LLC, Eden Prairie, MN (US)

(72) Inventors: Christopher A. Thierfelder, Minneapolis, MN (US); John W. Westrum, Jr., Prior Lake, MN (US)

(73) Assignee: Astora Women's Health, LLC, Minnetonka, MN (US)

( * ) Notice: Subject to any disclaimer, the term of this patent is extended or adjusted under 35 U.S.C. 154(b) by 234 days.

This patent is subject to a terminal disclaimer.

(21) Appl. No.: 14/967,730

(22) Filed: Dec. 14, 2015

(65) Prior Publication Data

US 2016/0095686 A1    Apr. 7, 2016

Related U.S. Application Data

(60) Continuation of application No. 14/532,576, filed on Nov. 4, 2014, now Pat. No. 9,211,177, which is a
(Continued)

(51) Int. Cl.
*A61F 2/02* (2006.01)
*A61F 2/00* (2006.01)
(Continued)

(52) U.S. Cl.
CPC ...... *A61F 2/0045* (2013.01); *A61B 17/00234* (2013.01); *A61B 17/0401* (2013.01); *A61B 17/06109* (2013.01); *A61F 2/0036* (2013.01); *A61F 2/0063* (2013.01); *A61B 2017/00805* (2013.01); *A61F 2002/0072* (2013.01); *A61F 2230/006* (2013.01); *A61F 2250/0012* (2013.01); *A61F 2250/0059* (2013.01); *A61F 2250/0078* (2013.01)

(58) Field of Classification Search
CPC ............ A61F 2/0063; A61F 2002/0072; A61F 2/0004; A61F 2/0036; A61F 2/0045; A61F 17/0619; A61F 17/00234
USPC ........... 600/29–32; 128/DIG. 25; 607/65–67, 607/72–75, 119, 148
See application file for complete search history.

(56) References Cited

U.S. PATENT DOCUMENTS 3,077,879 A   2/1963 Knoch
3,747,603 A   7/1973 Adler
(Continued)

FOREIGN PATENT DOCUMENTS

DE   196 13 317 A1   10/1996
EP    0 159 502 A2   10/1985
(Continued)

OTHER PUBLICATIONS

U.S. Appl. No. 60/356,697, Jacquetin.
(Continued)

*Primary Examiner* — John Lacyk
(74) *Attorney, Agent, or Firm* — Kagan Binder, PLLC

(57) ABSTRACT

An implantable article and method are disclosed for treating pelvic floor disorders such as vaginal vault prolase. A surgical kit useful for performing a surgical procedure such as a sacral colpopexy is also described.

12 Claims, 11 Drawing Sheets

Related U.S. Application Data continuation of application No. 13/873,983, filed on Apr. 30, 2013, now Pat. No. 8,905,912, which is a continuation of application No. 13/252,324, filed on Oct. 4, 2011, now Pat. No. 8,702,586, which is a continuation of application No. 11/983,412, filed on Nov. 7, 2007, now Pat. No. 8,057,382, which is a continuation of application No. 10/873,472, filed on Jun. 22, 2004, now Pat. No. 7,517,313, which is a continuation of application No. 10/431,719, filed on May 8, 2003, now Pat. No. 6,884,212, which is a division of application No. 09/939,282, filed on Aug. 24, 2001, now Pat. No. 6,592,515.

(60) Provisional application No. 60/269,828, filed on Feb. 20, 2001, provisional application No. 60/230,647, filed on Sep. 7, 2000.

(51) Int. Cl.
*A61B 17/00* (2006.01)
*A61B 17/04* (2006.01)
*A61B 17/06* (2006.01)

(56) References Cited

U.S. PATENT DOCUMENTS

| | | |
|---|---|---|
| 3,809,091 A | 5/1974 | Shute |
| 4,202,480 A | 5/1980 | Annett |
| 4,312,337 A | 1/1982 | Donohue |
| 4,347,847 A | 9/1982 | Usher |
| 4,520,821 A | 6/1985 | Schmidt et al. |
| 4,527,725 A | 7/1985 | Foslien |
| 4,655,221 A | 4/1987 | Devereux |
| 4,769,038 A | 9/1988 | Bendavid et al. |
| 4,938,760 A | 7/1990 | Burton et al. |
| 4,941,466 A | 7/1990 | Romano |
| 4,969,892 A | 11/1990 | Burton et al. |
| 5,080,664 A | 1/1992 | Jain |
| 5,112,344 A | 5/1992 | Petros |
| 5,147,387 A | 9/1992 | Jansen et al. |
| 5,195,542 A | 3/1993 | Gazielly et al. |
| 5,222,987 A | 6/1993 | Jones |
| 5,290,217 A | 3/1994 | Campos |
| 5,328,077 A | 7/1994 | Lou |
| 5,330,479 A | 7/1994 | Whitmore |
| 5,342,384 A | 8/1994 | Sugarbaker |
| 5,360,628 A | 11/1994 | Butland |
| 5,362,294 A | 11/1994 | Seitzinger |
| 5,404,870 A | 4/1995 | Brinkerhoff et al. |
| 5,441,508 A | 8/1995 | Gazielly et al. |
| 5,509,918 A | 4/1996 | Romano |
| 5,520,700 A | 5/1996 | Beyar et al. |
| 5,569,273 A | 10/1996 | Titone et al. |
| 5,611,515 A | 3/1997 | Benderev et al. |
| 5,657,648 A | 8/1997 | Ives et al. |
| 5,658,307 A | 8/1997 | Exconde |
| 5,674,247 A | 10/1997 | Sohn |
| 5,681,325 A | 10/1997 | Hasson |
| 5,681,340 A | 10/1997 | Veronikis |
| 5,738,628 A | 4/1998 | Sierocuk et al. |
| 5,746,749 A | 5/1998 | Willard |
| 5,756,145 A | 5/1998 | Darouiche |
| 5,807,403 A | 9/1998 | Beyar et al. |
| 5,836,503 A | 11/1998 | Ehrenfels et al. |
| 5,840,011 A | 11/1998 | Landgrebe et al. |
| 5,842,478 A | 12/1998 | Benderev et al. |
| 5,860,425 A | 1/1999 | Benderev et al. |
| 5,873,891 A | 2/1999 | Sohn |
| 5,899,909 A | 5/1999 | Claren et al. |
| 5,922,026 A | 7/1999 | Chin |
| 5,934,283 A | 8/1999 | Willem et al. |
| 5,972,000 A | 10/1999 | Beyar et al. |
| 6,039,686 A | 3/2000 | Kovac |
| 6,042,534 A | 3/2000 | Gellman et al. |
| 6,042,536 A | 3/2000 | Rydell et al. |
| 6,045,571 A | 4/2000 | Hill et al. |
| 6,068,591 A | 5/2000 | Bruckner et al. |
| 6,090,116 A | 7/2000 | D'Aversa et al. |
| 6,110,101 A | 8/2000 | Tihon et al. |
| 6,120,539 A | 9/2000 | Eldridge et al. |
| 6,162,487 A | 12/2000 | Darouiche |
| 6,162,962 A | 12/2000 | Hinsch et al. |
| 6,183,499 B1 | 2/2001 | Fisher et al. |
| 6,264,702 B1 | 7/2001 | Ory et al. |
| 6,306,079 B1 | 10/2001 | Trabucco |
| 6,530,943 B1 | 3/2003 | Hoepffner et al. |
| 6,612,977 B2 | 3/2003 | Staskin et al. |
| 6,592,515 B2 * | 7/2003 | Thierfelder ...... A61B 17/00234 600/37 |
| 6,641,525 B2 | 11/2003 | Rocheleau et al. |
| 6,652,450 B2 | 11/2003 | Neisz et al. |
| 6,691,711 B2 | 2/2004 | Raz et al. |
| 6,884,212 B2 * | 4/2005 | Thierfelder ...... A61B 17/00234 600/30 |
| 7,517,313 B2 * | 4/2009 | Thierfelder ...... A61B 17/00234 600/30 |
| 8,057,382 B2 * | 11/2011 | Thierfelder ...... A61B 17/00234 600/30 |
| 8,702,586 B2 * | 4/2014 | Thierfelder ...... A61B 17/00234 600/30 |
| 8,905,912 B2 * | 12/2014 | Thierfelder ...... A61B 17/00234 600/30 |
| 9,022,921 B2 * | 5/2015 | Thiefelder ....... A61B 17/00234 600/30 |
| 9,211,177 B2 * | 12/2015 | Thiefelder ....... A61B 17/00234 600/30 |
| 2001/0018549 A1 | 8/2001 | Snitkin et al. |
| 2002/0072694 A1 | 6/2002 | Therin |
| 2003/0004395 A1 | 1/2003 | Gellman |
| 2003/0023137 A1 | 1/2003 | Ulmsten et al. |
| 2003/0114866 A1 | 6/2003 | Kammerer |
| 2003/0176762 A1 | 9/2003 | Jacquetin |
| 2003/0220538 A1 | 11/2003 | Kammerer |

FOREIGN PATENT DOCUMENTS

| | | |
|---|---|---|
| EP | 0 265 157 A1 | 4/1988 |
| EP | 0 470 308 A1 | 8/1990 |
| FR | 2 737 106 A1 | 1/1997 |
| WO | WO 92/06638 | 4/1992 |
| WO | WO 93/17635 | 9/1993 |
| WO | WO 97/47246 | 12/1997 |
| WO | WO 98/14134 | 4/1998 |
| WO | WO 98/58598 A | 12/1998 |
| WO | WO 00/27304 | 5/2000 |
| WO | WO 00/57812 | 10/2000 |
| WO | WO 00/64370 | 11/2000 |
| WO | WO 00/74578 A2 | 12/2000 |
| WO | WO 00/74594 A1 | 12/2000 |
| WO | WO 01/39670 A1 | 6/2001 |
| WO | WO 02/28312 A1 | 4/2002 |

OTHER PUBLICATIONS

U.S. Appl. No. 60/361,503, Snitkin et al.

Costantini, E., et al., Colposacropexy With Gore-Tex Mesh in Marked Vaginal and Uterovaginal Prolapse, European Urology, pp. 111-117 (1998).

Geomini, Peggy et al., Vaginal Vault Suspension by Abdominal Sacral Colpopexy for Prolapse: A Follow Up Study of 40 Patients, European Journal of Obstetrics & Gynecology and Reproductive Biology, pp. 234-238 (2001).

Lienemann, Andreas, et al., Functional Cine Magnetic Resonance Imaging in Women After Abdominal Sacrocolpopexy, Obstetrics & Gynecology, pp. 81-85 vol. 97, No1 1 (Jan. 2001).

Massimo, Diana et al., Treatment of Vaginal Vault Prolaps With Abdominal Sacral Colpopexy Using Prolene Mesh, American Journal of Surgery, vol. 179, pp. 126-128 (Feb. 2000).

Nichols, David, Sacrospinous Fixation for Massive Eversion of the Vagina, Am J. Obstet. Gynecol., pp. 901-904 (Apr. 1, 1982).

(56) References Cited

OTHER PUBLICATIONS

Nichols, David & Randall, Clyde, Massive Eversion of the Vagina, Vaginal Surgery, pp. 351-383 Chapter 16, (4th ed. 1996).
Paraiso, M.F.R. et al., Laparoscopic Surgery for Enterocele, Vaginal Apex Prolapse and Rectocele, International Urogynecology Journal, vol. 10, pp. 223-229 (1999).
Rackley, Raymond, Synthetic Slings: Five Steps for Successful Placement, Urology Times, pp. 47-49 (Jun. 2000).
Richter, Kurt, Massive Eversion of the Vagina: Pathogenesis, Diagnosis, and Therapy of the "True" Prolapse of the Vaginal Stump, Clinical Obstetrics and Gyneocology, vol. 25 No. 4, p. 897-912 (Dec. 1982).
Stanton, Stuart, Vaginal Prolapse, Female Urology, pp. 229-241(1983).
Winters, C. et al., Abdominal Sacral Colpopexy and Abdominal Enterocele Repair in the Management of Vaginal Vault Prolapse, Urology 56, pp. 55-63 (2000).
Winters, C. et al., Use of Bone Anchors in Female Urology, Urology, pp. 15-22 (Dec. 2000).
Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).
Bassler, Kaven et al, Abdominal Sacrocolpopexy and Anatomy and Function of the Posterior Compartment, Obstetrics & Gynecology, vol. 97, n. 5, Part 1, pp. 678-684 (May 2001).
Cervigni, Mauro et al., The Use of Synthetics in the Treatment of Pelvic Organ Prolapse, Current Opinion in Urology, Voiding Dysfunction and Female Urology, vol. 11, pp. 429-435 (2001).
Dietz, H. P. et al, Mechanical Properties of Urogynecologic Implant Materials, Int Urogynecol J., vol. 14, pp. 239-243 (2003).
Farnsworth, B. N., Posterior Intravaginal Slingplasty (Infracoccygeal Sacropexy) for Severe Posthysterectomy Vaginal Vault Prolapse—A Preliminary Report on Efficacy and Safety, Int'l. Urogynecology Journal, vol. 13, pp. 4-8 (2002).
Farquhar, Cynthia M. et al., Hysterectomy Rates in the United States 1990-1997, Obstetrics & Gynecology, vol. 99, n. 2, pp. 229-234 (Feb. 2002).
Fidela, Marie R. et al., Pelvic Support Defects and Visceral and Sexual Function in Women Treated With Sacrospinous Ligament Suspension and Pelvic Reconstruction, Am J Obstet Gynecol, vol. 175, n. 6, 14 pages (Dec. 1996).
Flood, C.G. et al., Anterior Colporrhaphy Reinforced With Marlex Mesh for the Treatment of Cystoceles, Int Urogynecol J, vol. 9, pp. 200-204 (1998).
Handa, Victoria L. et al, Banked Human Fascia Lata for the Suburethral Sling Procedure: A Preliminary Report, Obstetrics & Gynecology, vol. 88, n. 6, pp. 1045-1049 (Dec. 1996).
Iglesia, C.B. et al., The Use of Mesh in Gynecologic Surgery, Int Urogyncol J, vol. 8, pp. 105-115 (1997).
Julian, Thomas, The Efficacy of Marlex Mesh in the Repair of Sever, Recurrent Vaginal Prolapse of the Anterior Midvaginal Wall, Am J Obset Gynecol, vol. 175, n. 6, pp. 1472-1475 (Dec. 1996).
Karram, Prolapse, Mickey M. et al., Chapter 19 Surgical Treatment of Vaginal Vault Prolapse, Urogynecology and Reconstructive Pelvic Surgery, (Walters & Karram eds.) pp. 235-256 (Mosby 1999).
Kersey, J., The Gauze Hammock Sling Operation in the Treatment of Stress Incontinence, British Journal of Obstetrics and Gynaecology, vol. 90, pp. 945-949 (Oct. 1983).
Luber, Karl M. et al., The Demographics of Pelvic Floor Disorders: Current Observations and Future Projections, Am J Obstet Gynecol, vol. 184, n. 7, pp. 1496-1503 (Jun. 2001).
Mage, Technique Chirurgicale, L'Interpostion D'un Treillis Synthetique Dans la Cure Par Voie Vaginale des Prolapsus Genitaux, J Gynecol Obstet Biol Reprod, vol. 28, pp. 825-829 (1999) (English Summary).
Marchionni, Mauro et al., True Incidence of Vaginal Vault Prolapse—Thirteen Years of Experience, The Journal of Reproductive Medicine, vol. 44, n. 8, pp. 679-684 (Aug. 1999).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).
Migliari, Roberto et al., Tension-Free Vaginal Mesh Repair for Anterior Vaginal Wall Prolapse, Eur Urol, vol. 38, pp. 151-155 (2000).
Morgan, J. E, A Sling Operation, Using Marlex Polypropylene Mesh, for Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1995).
Morley, George W. et al., Sacrospinous Ligament Fixation for Eversion of the Vagina, Am J Obstet Gyn, vol. 158, n. 4, pp. 872-881 (Apr. 1988).
Mouly, Patrick et al., Vaginal Reconstruction of a Complete Vaginal Prolapse: The Trans Obturator Repair, The Journal of Urology, vol. 169, No. 4, Suppl., V702, p. 182 (Apr. 2003).
Nichols, David H., The Mersilene Mesh Gauze-Hammock for Severe Urinary Stress Incontinence, Obstetrics and Gynecology, vol. 41, pp. 88-93 (Jan. 1973).
Nicita, Giulio, A New Operation for Genitourinary Prolapse, Journal of Urology, vol. 160, pp. 741-745 (Sep. 1998).
Petros, PE Papa, The Intravaginal Slingplasty Operation, A Minimally Invasive Technique for Cure of Urinary Incontinence in the Female, Aust. NZ J Obstet Gynaecol, vol. 36, n. 4, pp. 453-461 (1996).
Petros, P. E. Papa, Vault Prolapse II; Restoration of Dynamic Vaginal Supports by Infracoccygeal Sacropexy, an Axial Day-Case Vaginal Procedure, Int Urogynecol J, vol. 12, pp. 296-303 (2001).
Petros, P. E. Papa, Development of Generic Models for Ambulatory Vaginal Surgery—Preliminary Report, Int Urogynecol J, pp. 20-27 (1998).
Petros, Peter E. Papa et al., Urethral Pressure Increase on Effort Originates From Within the Urethra, and Continence From Musculovaginal Closure, Neurourology and Urodynamics, vol. 14, pp. 337-350 (1995).
Petros, Peter E. Papa et al., The Tethered Vagina Syndrome, Post Surgical Incontinence and I-Plasty Operation for Cure, Acta Obstet Gynecol Scand, vol. 69, Suppl 153, pp. 63-67 (1990).
Salomon, L. J. et al., Treatment of Anterior Vaginal Wall Prolapse With Porcine Skin Collagen Implant by the Transobturator Route: Preliminary Results, European Urology, vol. 45, pp. 219-225 (2004).
Sanz, Luis E. et al., Modification of Abdominal Sacrocolpopexy Using a Suture Anchor System, The Journal of Reproductive Medicine, vol. 48, n. 7, pp. 496-500 (Jul. 2003).
Sergent, F. et al., Prosthetic Restoration of the Pelvic Diaphragm in Genital Urinary Prolapse Surgery: Transobturator and Infracoccygeal Hammock Technique, J Gynecol Obstet Biol Reprod, vol. 32, No. 2, pp. 120-126 (Apr. 2003).
Subak, Leslee L. et al., Cost of Pelvic Organ Prolapse Surgery in the United States, Obstetrics & Gynecology, vol. 98, n. 4, pp. 646-651 (Oct. 2001).
Sullivan, Eugene S. et al., Total Pelvic Mesh Repair, A Ten-Year Experience, Dis. Colon Rectum, vol. 44, No. 8, pp. 857-863 (Jun. 2001).
Swift, S.E., et al., Case-Control Study of Etiologic Factors in the Development of Severe Pelvic Organ Prolapse, Int Urogynecol J, vol. 12, pp. 187-192 (2001).
Visco, Anthony G. et al., Vaginal Mesh Erosion After Abdominal Sacral Colpopexy, Am J Obstet Gynecol, vol. 184, n. 3, pp. 297-302 (Feb. 2001).
Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).
Zacharin, Robert F. et al., Pulsion Enterocele: Long-Term Results of an Abdominoperineal Technique, Obstetrics & Gynecology, vol. 55 No. 2, pp. 141-148 (Feb. 1980).
"We're staying ahead of the curve", Introducing the IVS Tunneller Device for Tension Free Procedures, Tyco Healthcare, 3 pages (2002).

(56) References Cited

OTHER PUBLICATIONS

Comparison of Tissue Reaction of Monofilament and Multifilament Polypropylene Mesh—A Case Report, Tyco Healthcare, United States Surgical, 4 pages (2002).

* cited by examiner

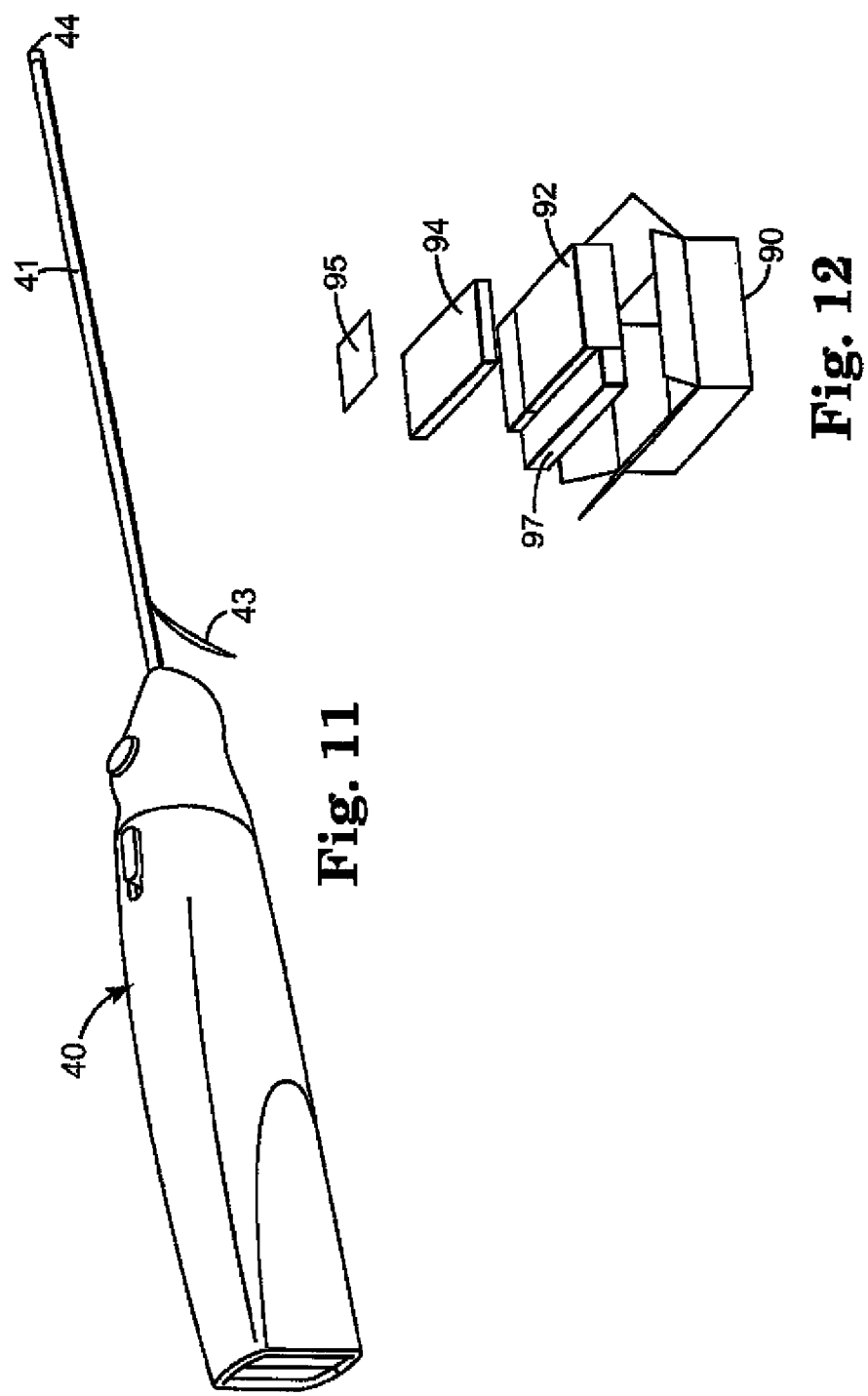

IMPLANTABLE ARTICLE AND METHOD

CROSS REFERENCE TO RELATED APPLICATIONS

This application is a continuation of U.S. application Ser. No. 14/532,576, filed Nov. 4, 2014, which is a continuation of U.S. application Ser. No. 13/873,983, filed Apr. 30, 2013, which is a continuation of U.S. application Ser. No. 13/252,324, filed Oct. 4, 2011, now U.S. Pat. No. 8,702,586, which is a continuation of U.S. application Ser. No. 11/983,412, filed Nov. 7, 2007, now U.S. Pat. No. 8,057,382, which is a continuation of U.S. application Ser. No. 10/873,472, filed Jun. 22, 2004, now U.S. Pat. No. 7,517,313, which is a continuation of U.S. application Ser. No. 10/431,719, filed May 8, 2003, now U.S. Pat. No. 6,884,212, which is a divisional of U.S. application Ser. No. 09/939,282, filed Aug. 24, 2001, now U.S. Pat. No. 6,592,515, which claims the benefit of U.S. Provisional Patent Application No. 60/230,647, filed Sep. 7, 2000 and U.S. Provisional Application Ser. No. 60/269,828, filed Feb. 20, 2001, all of which are hereby incorporated by reference in their entireties.

BACKGROUND

There are a variety of materials approved by regulatory agencies for implantation into the human body. Examples of such materials include Trelex Polypropylene Mesh, available from Boston Scientific of Minneapolis Minn.), Marlex Mesh (polypropylene suture material, available from Phillips Sumika Polypropylene Co., Houston, Tex.), Prolene™ Mesh (available from Ethicon, Inc. of Sommerville, N.J.), Mersilene material (polyester fibermesh) and Gore-Tex fabric (expanded polytetrafluoroethylene laminated fabric, available from W.L. Gore and Associates Inc., Elkton, Md.). Many of these materials are integrated into devices that are implanted in the body. As a commercial example, silicone covered polyester is used as a component of an Artificial Urinary Sphincter model #800, available from American Medical Systems, Inc. of Minnetonka, Minn.

Pelvic floor disorders include cystocele, rectocele, enterocele and uterine and vaginal vault prolapse. These disorders typically result from weakness or damage to normal pelvic support systems. The most common etiologies include childbearing, removal of the uterus, connective tissue defects, prolonged heavy physical labor and postmenopausal atrophy.

Vaginal vault prolapse is the distension of the vaginal apex outside of the vagina. An enterocele is a vaginal hernia in which the peritoneal sac containing a portion of the small bowel extends into the rectovaginal space. Vaginal vault prolapse and enterocele represent challenging forms of pelvic disorders for surgeons.

Vaginal vault prolapse is often associated with a rectocele, cystocele or enterocele. It is known to repair vaginal vault prolapse by suturing to the supraspinous ligament or to attach the vaginal vault through mesh or fascia to the sacrum. Many patients suffering from vaginal vault prolapse also require a surgical procedure to correct stress urinary incontinence that is either symptomatic or latent.

Sling procedures are surgical methods that place a sling to stabilize or support the bladder neck or urethra. They are typically used to treat incontinence. There are a variety of different sling procedures. Slings used for pubovaginal procedures differ in the type of material and anchoring methods. In some cases, the sling is placed under the bladder neck and secured via suspension sutures to a point of attachment (e.g. bone) through an abdominal and/or vaginal incision. Examples of sling procedures are disclosed in U.S. Pat. Nos. 5,112,344; 5,611,515; 5,842,478; 5,860,425; 5,899,909; 6,039,686, 6,042,534 and 6,110,101.

A sacral colpopexy is a procedure for providing vaginal vault suspension. It may be performed through an abdominal incision, a vaginal incision or laparoscopically. Complications include mesh infection, mesh erosion, bowel obstruction, ileus, and bleeding from the presacral venous complex. Typically, this procedure is accompanied by an abdominal enterocele repair and cul-de-sac obliteration.

A sacral colpopexy entails suspension of the vaginal cuff to the sacrum with fascia or synthetic mesh. The synthetic mesh is typically carefully customized or assembled into a special shape by the surgeon. A surgeon manually cuts a sheet of the mesh and stitches elements of the mesh to form the special shape. The literature reports surgeons suturing mesh material into various T-shaped articles. See Winters et al., *Abdominal Sacral Colpopexy and Abdominal Enterocele Repair in the Management of Vaginal Vault Prolapse*, Urology 56 (Suppl 6A) (2000): 55-63; and Paraiso et al, *Laparoscopic Surgery for Enterocele, Vaginal Apex Prolapse and Rectocele*, Int Urogynecol J (1999), 10:223-229.

Suturing mesh material into T-shaped articles is a meticulous, time-consuming task. Valuable surgeon time is consumed during this task. It is reported that the average time for colpopexy and enterocele repair alone is at least 20 minutes and more likely approximately ninety minutes. It is reported that 72% of patients with vault prolapse had a combination of other pelvic floor defects. See Richter K: *Massive Eversion of the Vagina: Pathogenesis, Diagnosis and Therapy of the True Prolapse of the Vaginal Stump*, Clin. Obstet Gynecol 25:897-912 (1982). If surgical correction of cystocele, rectocele or stress incontinence is performed in the presence of untreated vaginal vault prolapse, an early recurrence of prolapse is extremely likely. When it is considered that it is often necessary to correct multiple pelvic floor disorders simultaneously, the time factor for surgeons is particularly challenging. See, Diana et al., *Treatment of Vaginal Vault Prolapse with Abdominal Sacral Colpopexy Using Prolene Mesh*, American Journal of Surgery, Vol. 179, (February 2000), Pps. 126-128.

U.S. Pat. No. 6,264,702 describes a prosthesis for preventing post-surgical adhesions. The prosthesis may be used in visceral, parietal or neurological surgery, particularly hernia repair.

U.S. Pat. No. 4,655,221 discloses a surgical repair mesh and a method of using a surgical repair mesh.

PCT Publication No. WO 00/64370 (Gaston) describes a device for treating a prolapse by vaginal suspension. The device comprises an elongate, flexible, pierced material, a suture connected to the material and a suture needle joined to the suture. The device is long enough to enable posterior suspension of the vagina at the promontory (i.e. the front upper part of the sacrum). The other end of the device includes a distal portion having a width such that it can cover at least a large part of the posterior part of the vagina, a rounded cut-out with dimensions that enable it to be engaged around the base of the vagina on at least a large part of the lower half of the wall of the vagina. The suture is connected to the article so that it is offset sidewise in relation to the cut-out.

U.S. Pat. No. 6,162,962 discloses an areal implant, in particular for abdominal wall closure. The implantable article may be constructed from a knitted fabric comprising a non-resorbable or slowly resorbable material.

U.S. Pat. No. 4,769,038 discloses prostheses for repair of inguinal and femoral hernias. FIG. 1 of that patent illustrates a three panel inguinal prosthesis.

U.S. Pat. Nos. 5,195,542 and 5,441,508 (Gazielly et al.) disclose a rotator cuff reinforcement strip for surgical implantation to a shoulder of a person. In one embodiment, the strip has a rear heel for fixation to at least one of a trochiter and a tendinous mass of the patient's rotator cuff. The strip may have a linear extension or divergent legs from the heel defining opposite ends for fixation to respective tendon(s) of the rotator cuff. In one embodiment, the strip is described as defining a Y-shape. The device may consist of a single layer of braided polypropylene material.

PCT Publication No. WO 00/27304 (ORY et al.) discloses a suspension device for treating prolapse and urinary incontinence. The device comprises at least one filiform suspension cord with limited elasticity and at least two anchoring parts linked to the ends of the cord.

BRIEF SUMMARY

The present invention is directed to a preassembled implantable article suitable for a variety of surgical procedures, preferably urological procedures and more particularly to those directed to pelvic floor disorders. The preassembled implantable article reduces the challenge faced by the surgeon by eliminating the need to meticulously create a customized implantable article for such surgical procedures.

In one aspect, the present invention comprises an implantable surgical article comprising a thin, substantially flat major strip having proximal and distal ends, and a length and a width along first and second orthogonal axes, and a thin, substantially flat minor strip having a length less than that of the major strip, and a pair of ends. The minor strip is bonded to the major strip along an end of the minor portion such that a substantial portion of the minor strip can extend along an axis that is perpendicular to both the first and second axes. The location of the bond is preferably selected such that a portion of the major strip near its distal end and the minor strip may be sutured to a vaginal cuff of a patient. The distance between the proximal end of the major strip and the bond is at least sufficient to extend from the patient's sacrum to the vaginal cuff.

Preferably, the straight edges of the major and minor strips are substantially aligned to provide a surgical article with a substantially constant width. Also preferably, the minor strip is bonded to the major strip along substantially all of the end of the minor strip. More preferably, the distal ends of the major and minor strips are substantially aligned.

Alternatively, the invention may be viewed as an implantable surgical article for treating a pelvic floor disorder, such as for a sacral colpopexy procedure. The article comprises a base portion, a head portion comprising two tissue engagement portions extending from the base portion, and separation force distribution means for attaching at least one of the tissue engagement portions to the base portion in a fashion that distributes a force that would tend to separate a tissue engagement portion from the base portion across an area greater than that occupied by a suture.

The separation force distribution means may comprise a variety of means, such as a bonding composition (e.g. an elastomeric material), a tissue adhesive, a tissue sealant, an ultrasonic weld, or a mechanical fastener (e.g. a polymeric clip).

The article may have other optional features. For example, the article may include means for adjusting the tension of the implantable article. The means may include wheels rotatably associated with a clip that also attaches the base portion of the implant to the tissue engagement portions. Optionally, the tension adjustment means may comprise a means for indexing the wheel between a plurality of positions. In one embodiment, the tension adjustment means may comprises a ratchet wheel, pawl and spring assembly.

The surgical article preferably comprises a backing and a coating. In one embodiment, the backing comprises a polymeric material or fabric and the coating comprises a silicone. After coating, the surgical article preferably remains porous to afford tissue ingrowth. Preferably, if the implantable article is to be used in a sacral colpopexy procedure, the implantable article is sized and shaped to loosely extend from the patient's sacrum to the patient's vagina with at least some slack.

Alternatively, portions of the implantable article (e.g. the base portion) may comprise suture bridges instead of fabric or substantially flat, planar structures.

In another aspect, the present invention comprises a surgical kit for use in a procedure for addressing a pelvic floor disorder. The surgical kit comprises a preassembled implantable article having a base portion, securement means for securing the base portion of the implantable article to tissue, and a surgical article far inserting the securement means into tissue. Preferably, the kit includes a Y-shaped article that is sized and shaped to treat vaginal vault prolapse during a sacral colpopexy procedure.

In the context of a surgical kit of the present invention, the implantable article is preassembled, that is, its is substantially completely constructed prior to the surgical procedure. By "substantially completely constructed", it is contemplated that the surgeon may still have to trim redundant portions of the implantable article during the surgical procedure. For example, for a small patient, some of the base portion may be trimmed from the surgical article by the surgeon just before implantation.

The preassembled implantable article is preferably preassembled in a V-shape and is sterile packaged. In the context of a kit according to the present invention, the implantable article may preassembled by any suitable means including adhesives, bonding agents, tissue sealants, sutures or mechanical fasteners.

Preferably, the securement means comprises a bone anchor with associated sutures (e.g. braided or monofilaments), self tapping screws, darts or the like. Alternatively, the securement means may comprise sutures suitable for implantation into bone.

The surgical article may comprise a powered (e.g. battery, plug-in, compressed fluid, etc.) surgical instrument or a manual surgical instrument. Preferably, the surgical article comprises a motorized surgical driver having a shaft. Preferably, the shaft is sized and shaped to extend from the abdomen of a patient to the sacrum. Alternatively, the surgical article may comprise a needle capable of placing a suture in bone, or a needle suitable for placing a suture in ligament or a needle suitable for placing a suture in soft tissue.

In another aspect the present invention comprises a method of making an implantable surgical article. The method comprises the steps of 1) providing a thin, first strip with first and second ends, major surfaces, and a length between the first and second ends; 2) providing a thin, second strip with first and second ends, major surfaces, and a length between the first and second ends; the length of the second strip being less than that of the first strip; 3) placing a major surface of the first strip against a major surface of the second strip; and 4) bonding the first strip to the second strip.

Preferably, the step of bonding the first strip to the second strip includes the step of bonding the first strip to the second strip with a silicone elastomer.

In one embodiment, the method preferably further includes the step of providing a fixture with a recessed portion, and the step of placing a major surface of the first strip against a major surface of the second strip includes the step of placing at least a portion of the first and second strips in the recessed portion of the fixture. In this embodiment, the step of bonding includes the step of bonding the portion of the first strip within the recessed portion to the portion of the second strip within the recessed portion. Liquid silicone is preferably injected into the recessed portion of the fixture.

Additional steps may be optionally incorporated in the method of the present invention. For example, silicone could be cured with heating means and excess silicone within pores may be removed by blowing compressed air on the article during the procedure.

BRIEF DESCRIPTION OF THE DRAWINGS

Other features and advantages of the present invention will be seen as the following description of particular embodiments progresses in conjunction with the drawings, in which:

FIG. 11 is a perspective view of a surgical article for use in a kit according to an aspect of the present invention;

FIG. 12 is a schematic view of a surgical kit assembly according to an aspect of the present invention;

DETAILED DESCRIPTION

The following description is meant to be illustrative only and not limiting. Other embodiments of this invention will be apparent to those of ordinary skill in the art in view of this description.

Figure 1:
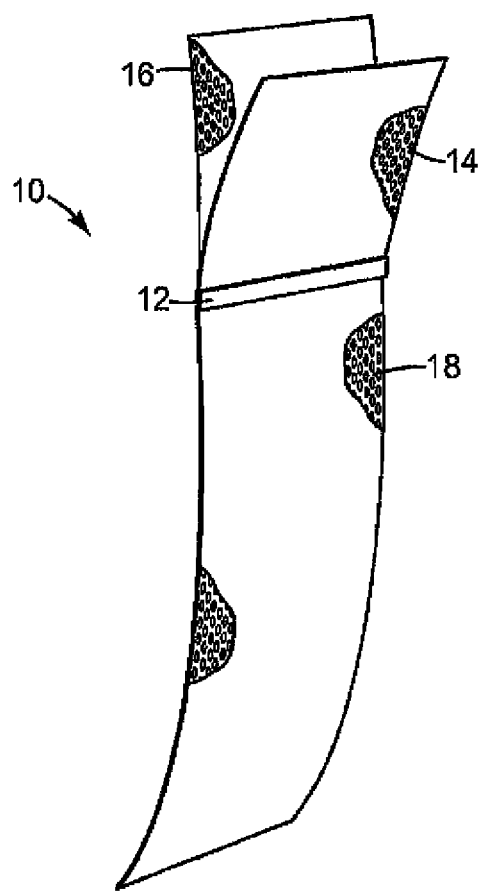
FIG. 1 is a perspective view of one embodiment of implantable article according to the present invention.

FIG. 1 illustrates an embodiment of implantable article 10 according to one aspect of the present invention. The implantable article of the present invention may generally be used in a variety of surgical procedures, preferably surgical procedures directed toward addressing urological disorders, and more preferably to surgical procedures for addressing pelvic floor disorders such as prolapse (e.g. vaginal), enteroceles (e.g. of the uterus), rectoceles and cystoceles. Non-urological procedures such as eventration or hernia repair, and visceral, parietal and neurological procedures are also included within the scope of the present invention. In a preferred embodiment, the implantable article 10 is used in a sacral colpopexy procedure. It is contemplated that the present invention may also be utilized in conjunction with other procedures, such as, but not limited to culposuspension, culdoplasty, procedures for addressing cystocele prolapse, and other surgical procedures that utilize an implantable article.

The dimensions of the implantable article will depend upon a variety of factors including the intended surgical uses. Preferably, for a sacral colpopexy procedure, the dimensions are at least sufficient to extend from the sacrum to the vaginal apex with additional size to account for the imprecision associated with the range of human anatomy sizes and for a small amount of slack. In a preferred embodiment, the maximum width of the implantable article is between about 1 and 6 centimeters, the overall length is between about 10 and 20 cm, and the thickness is between about 0.020 inches (0.508 mm) and 0.040 inches (1.016 mm). More preferably, the overall length is between about 17 cm and 17.4 cm., the width is about 4 cm and the thickness is between about 0.024 inches (0.61 mm) to about 0.036 inches (0.914 mm).

FIG. 1 illustrates a preferred embodiment of implantable article 10 according to the present invention. The article 10 comprises a base portion 18 and a head portion comprising a first tissue engagement portion 14 and a second tissue engagement portion 16. Each of the portions 14 and 16 extend from the base portion 18.

The implantable article 10 preferably includes separation force distribution means 12 for attaching at least one of the tissue engagement portions (e.g. portion 14) to the base portion 18 in a fashion that distributes a force that would tend to separate the tissue engagement portion 14 from the base portion 18 over a relatively wide area, as opposed to merely a suture that would tend to concentrate such a force at the location of the suture.

The means 12 preferably comprises any suitable material or assembly of materials. Preferably the material or the assembly of materials is biocompatible. Examples of suitable compositions include tissue adhesives, tissue sealants, biocompatible bonding agents (e.g. silicone), and biocompatible adhesives. Alternatively, RF or ultrasonic welding or heat sealing may be used alone or in conjunction with other techniques to create the separation force distribution means.

In a preferred embodiment, the implantable article has a plurality of pores that afford tissue ingrowth and resist infection. Preferably, the implantable article 10 comprises a backing that is coated. The backing material may comprise one or more woven, knitted or inter-linked filaments or fibers that form multiple fiber junctions. Monofilament and multi-filament embodiments are within the scope of the present invention. The fiber junctions may be formed via weaving, bonding, ultrasonic welding, knitting or other junction forming techniques, including combinations thereof. In addition, the size of the resultant openings or pores of the implantable article 10 should be sufficient to allow tissue in-growth and fixation within surrounding tissue. As an example, not intended to be limiting, the holes may comprise elliptical or diamond shaped holes with a diagonal in the range of about 0.040 inches (1.016 mm) to about 0.055 inches (1.397 mm).

The implantable article 10 may be made of a variety of materials including, but not limited to, Prolene™, nylon, polypropylene, Deklene™, poly-L-lactide (PLLA), polyethylene glycol (PGA), polyester and any combination of materials. Depending on the desired treatment, the article 10 or portions thereof, may be absorbable, non-absorbable and/or resorbable.

Non-synthetic structures are also included within the scope of the invention. Other synthetic and non-synthetic materials suitable for use in the present invention include, but are not limited to, synthetic biomaterials, allografts, homografts, heterografts, autologous tissues, materials disclosed in U.S. Provisional Application Ser. No. 60/263,472, Ser. No. 60/281,350 and Ser. No. 60/295,068 (whose contents are fully incorporated herein by reference), synthetic materials (such as metallics, polymerics, and plastics) and any combination of such materials may also be used as an element of an implantable article of the present invention.

Specific examples of suitable synthetic materials for use in the present invention include, but are not limited to polypropylene, polyester, polyethylene, nylon, PLLA and PGA. Preferably, the material should cause minimal to no reaction with body tissues and fluids and indefinitely retain its particular material characteristics/properties. Portions or all of the material may be resorbable if consistent with the desired surgical procedure.

In another embodiment, the article 10 is a flexible, polypropylene monofilament that resists weakening or degradation when implanted within a patient. One such material is Marlex™ material. As another example, not intended to be limiting, the mesh may be woven polypropylene monofilament, knitted with a warp tricot.

In another embodiment of the invention, the implantable article 10 or portions thereof, may have one or more substances associated therewith through a process such as coating. Examples of appropriate substances include, without limitation, drugs, hormones, antibiotics, antimicrobial substances, dyes, silicone elastomers, acetal, polyurethanes, radiopaque filaments or substances, anti-bacterial substances, chemicals or agents, including any combinations thereof. The substances may be used to enhance treatment effects, reduce the potential for implantable article erosion or rejection by the body, enhance visualization, indicate proper sling orientation, resist infection, promote healing, increase softness or other desirable effects.

Optionally, a dye may be coated on one surface of the article 10 or a portion of the article 10 such as portion 14. The dye provides the practitioner/surgeon with a visual indicator to aid in properly orienting the article 10 at the target site within the patient. As another example, the article 10 may be coated by a process described in any of U.S. Pat. Nos. 5,624,704; 5,756,145; 5,853,745; 5,902,283 and 6,162,487 (the entire contents of which are hereby incorporated by reference).

Referring to FIG. 1, the base portion 18 is preferably, a thin, flexible structure that has a length and a width along first and second orthogonal axes that are much greater than the thickness of the base portion 18 (the thickness being measured along a third axis that is perpendicular to the first and second axes). The tissue engagement portions 14 and 16 are flexible and can extend along the third axis (i.e. the axis that is perpendicular to the first and second orthogonal axes) so that substantial structure may extend in three dimensions, as opposed to a flat, rectangular, prior art implant that only provides substantial structure in two dimensions. This allows the implantable article 10 to more readily conform to irregular, non-planar tissue surfaces such as the apex of the vagina.

Figure 2:
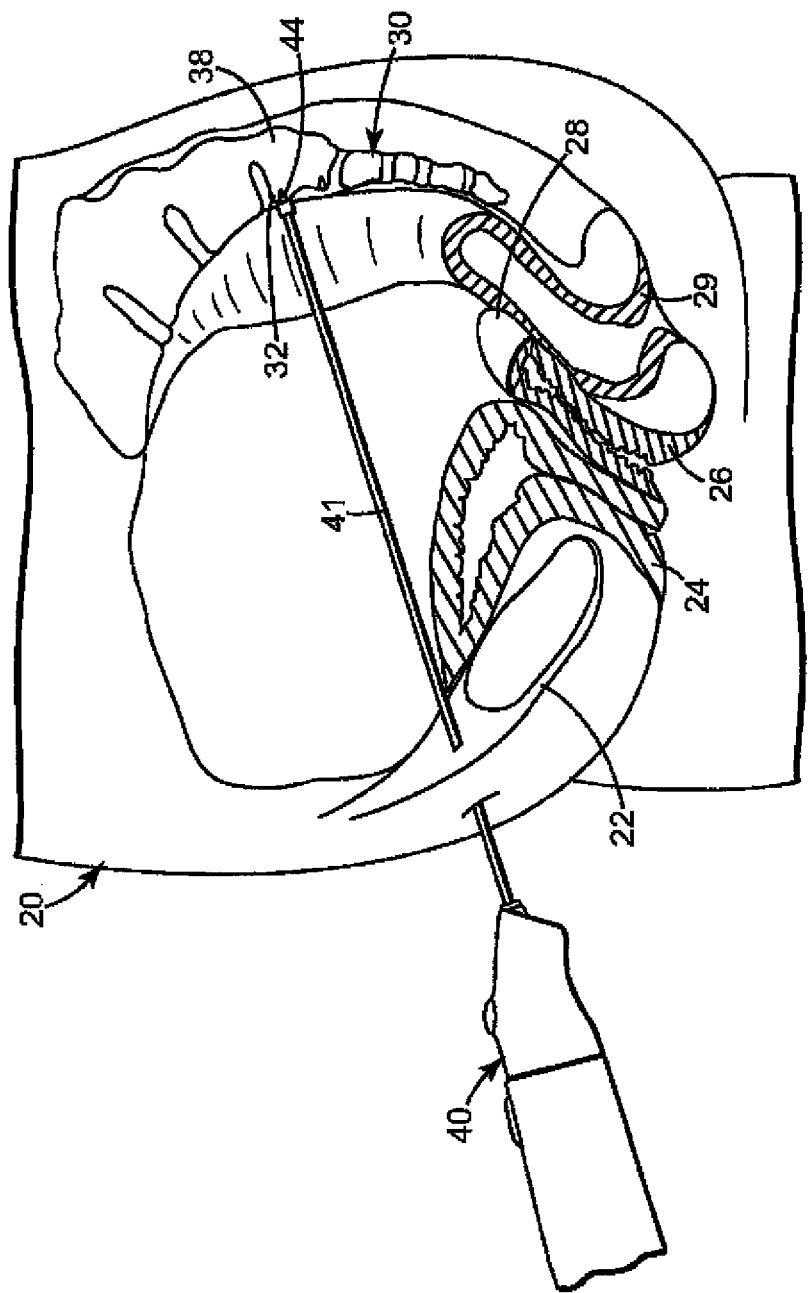
FIG. 2 is a schematic side view that illustrates a method of inserting a bone anchor in the sacrum according to an embodiment of the present invention.
Figure 3:
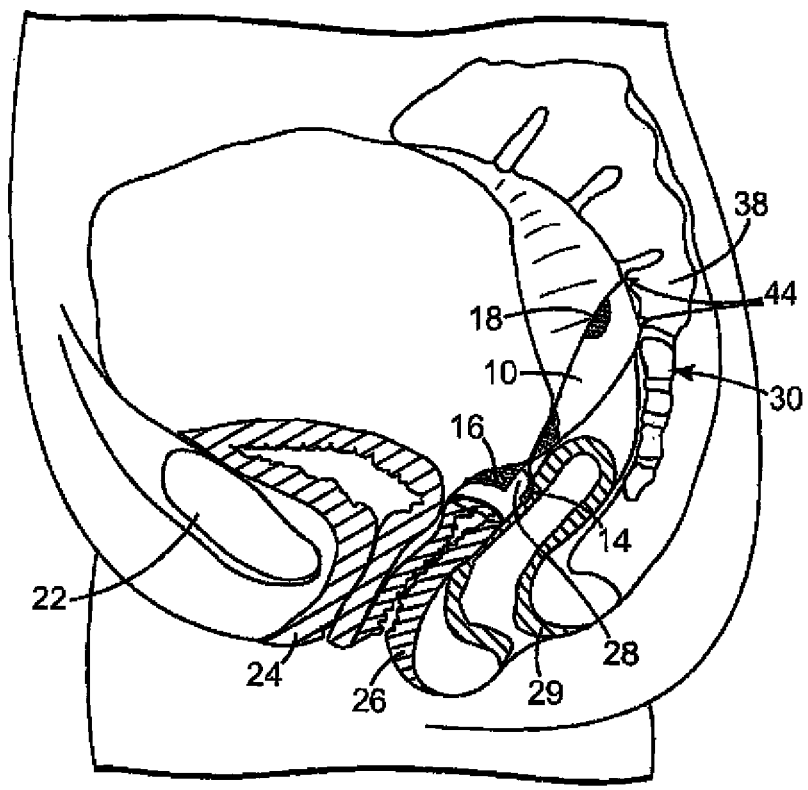
FIG. 3 is a schematic side view of the patient of FIG. 2 after the implantable article of FIG. 1 has been implanted.

FIGS. 2 and 3 schematically illustrate a surgical procedure that utilizes implantable article 10. FIG. 2 illustrates a powered surgical device 40 placing two bone screws 44 with attached sutures into the sacrum 30 of the patient 20. The vagina 28, sacrum 30, urethra 24, pelvic bone 22, vaginal cuff 28 and rectum 29 are shown schematically and should not be interpreted as being shown to scale or for anatomical precision.

Preferably, sacral segment three 38 is selected for the bone screws with attached sutures. The precise, final location of the implantable article 10 in the physiological environment will depend on a variety of factors including the particular surgical procedure(s) performed, the particular anatomy of the patient (e.g. the location of veins, nerves and arteries), and any preconditions of the patient such as scar tissue or previous surgeries. For a sacral colpopexy, sacral segment three 38 is preferred but other attachment locations are contemplated. Portions 14 and 16 of the implantable article 10 are sutured to the vagina cuff 28 and the base portion 18 of implantable article 10 is tied to the bone screws 44 by the sutures attached to the bone screws 44.

The implantable article 10 may optionally have a feature that assists the surgeon in placing the implantable article 10 in a therapeutically effective anatomical position. For example, it may be desirable to attach portion 14 of the implantable article 10 to the posterior side of the vaginal apex and the portion 16 to the anterior side of the vaginal apex. For this feature, a variety of means may be used. For example, portion 14 may be a different color than portion 16. Alternatively, indicia may be printed on portion 14 or 16 that indicates proper orientation.

In another aspect, the present invention comprises a surgical kit for use in a procedure for addressing a pelvic floor disorder such as a sacral colpopexy. Referring to FIG. 12, the surgical kit 90 comprises a preassembled implantable article (shown as being preassembled and packaged in a sterile package 94), securement means for securing the base portion of the implantable article to tissue (shown as within sterile package 95), and a surgical article for inserting the securement means into tissue (shown in sterile package 92).

The preassembled implantable article 94 preferably comprises an implantable article similar to that shown in FIG. 1 that includes a separation force distribution means 12 (e.g. a bond). It is noted that, in the context of the kit of the present invention, the preassembled implantable article 94 may comprise any implantable article with two or more elements preconnected together to form the implantable article. The specific means of connecting the two or more elements may comprise any suitable means including adhesives, bonding agents, mechanical fasteners (e.g. a medical grade plastic clip) or even sutures. Having a preassembled implantable article in a kit that is ready for use in a surgery saves valuable surgeon time and potentially reduces operation time.

The securement means 95 preferably comprises bone anchors. The bone anchors may comprise tacks, screws, bone sutures, staples, fasteners, pins, nails, headless screws, darts, or any suitable means for anchoring. More preferably, the bone anchors comprise self-tapping bone screws. More preferably, each bone screw has a suture attached thereto (e.g. a polypropylene monofilament). The sutures may be braided or a monofilament. The bone anchors may comprise those disclosed in any of U.S. Pat. Nos. 5,520,700, 5,674, 247; 5,807,403; 5,873,891; 5,972,000; and/or U.S. patent application Ser. No. 09/476,682, filed Dec. 30, 1999 (the entire contents of which are herein incorporated by reference). As an example, not intended to be limiting, the securement means may comprise medical grade titanium bone anchors with associated sutures. The sutures may comprise monofilament polypropylene or braided polyester or braided polyester coated with polytetrafluoroethylene (Teflon, PTFE), such as those generally available from Genzyme/Deknatel of Fall River, Ma.

Alternatively, the securement means in the kit may comprise tissue adhesive, tissue sealant, sutures (e.g. for implantation into bone), ligament sutures, bone tacks and other suitable elements.

The kit 90 also includes a sterile packaged surgical article 92 for use with the securement means. The surgical article (e.g. 40) within sterile package 92 is used to apply the securement means 95 during the surgical procedure. The surgical article may comprise any suitable surgical device. For example, the article may comprise a tissue adhesive dispenser, a tissue sealant dispenser or any of those articles described in U.S. patent application Ser. No. 09/476,682, filed Dec. 30, 1999; and/or U.S. Pat. Nos. 4,312,337; 4,941, 466; 5,330,479; and 5,509,918, and/or PCT International application no. PCT/IL 00/00320, filed Apr. 6, 2000; and/or PCT international publication nos. WO 97/47246 and 00/74578 (the entire contents of which are incorporated by reference).

FIG. 11 illustrates a preferred surgical article 40 for implanting a self tapping bone screw 44 having a suture 43 attached thereto. The surgical article 40 comprises a motorized driver having a shaft 41. The shaft 41 is preferably sized and shaped to extend from the abdomen of a patient to the sacrum. For example, the shaft may be approximately 28 cm in length or longer.

The surgical article 40 may be constructed in accordance with U.S. Pat. No. 5,520,700; and/or U.S. patent application Ser. No. 09/476,682; and/or Ser. No. 09/776,545, filed Feb. 2, 2001 (the entire contents of each of which is herein incorporated by reference). The surgical article 40 rotates the bone screw 44 to implant the bone screw 44 and attached suture 43.

The precise shape of the implantable article for the kit 90 will depend on a variety of factors including the desired therapeutic effect, the intended physiological environment for the implantable article, the surgical procedure and convenience. If the kit is used to treat vaginal prolapse in a sacral colpopexy procedure, the implantable article is preferably preassembled in a Y-shape. The article is preferably sized and shaped to loosely extend from the patient's sacrum to the patient's vagina with at least some slack.

Alternatively, instead of powered surgical driver 40, the surgical article within package 92 may comprise a needle capable of placing a suture in bone, soft tissue or in a ligament.

Figure 4:
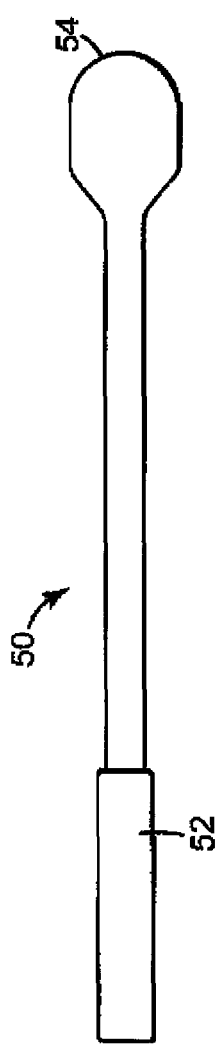
FIG. 4 is a side view of a vaginal distender for use in a surgical kit according to an aspect of the present invention.

The surgical kit 90 may include a variety of optional elements. For example, the kit may include a vaginal distender in sterile package 97. FIG. 4 illustrates a preferred embodiment of vaginal distender 50. Preferably, the vaginal distender is sized and shaped similar to a distender used in conjunction with a circular stapler in bowel surgery to create an end-to-end anastomosis.

The vaginal distender includes a handle portion 52 and an end portion 54 with a rounded, bulbous shape. The end portion is preferably constructed from material that allows a suture carrying needle to be driven through an implantable article, through vaginal tissue and against the end portion 54 so that the end portion 54 acts as an anvil-lice structure. As an example, not intended to be limiting, the maximum diameter of the end portion 54 may be about 1.25 inches (alternatively, e.g., 31 mm in diameter) and the handle portion may have a maximum diameter of about 0.625 inches. The distender assists the surgeon in attaching the implantable article circumferentially to the irregular shaped vaginal cuff, thereby reducing the potential for point stresses in the vagina.

Figure 5:
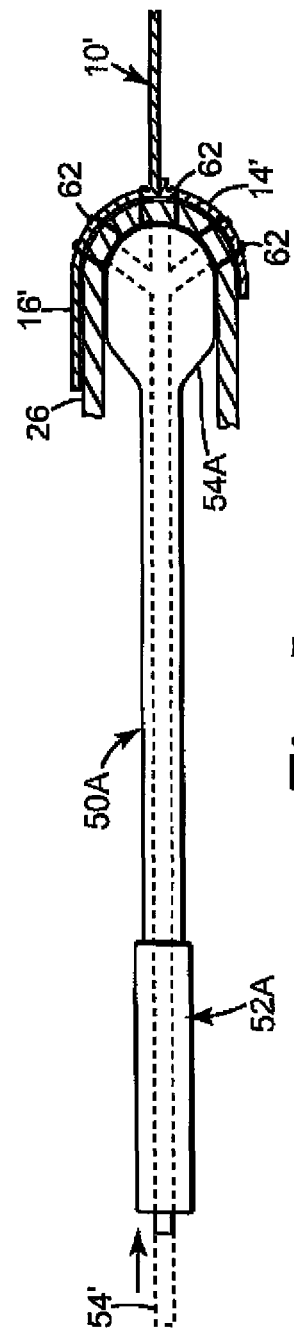
FIG. 5 is a side view of another embodiment, of distender according to another aspect of the present invention.

FIG. 5 illustrates another embodiment of optional distender 50A according to the present invention. The distender 50A may be utilized to attached a portion of an implantable article 10' to the vagina 26 of a patient. This distender 50A has the potential to reduce the invasiveness of the procedure. Alternatively, the distender 50A may be utilized to directly connect the vagina 26 to the sacrum of the patient. In this embodiment, the article 10 is not used. Instead, the vagina is stapled directly to the sacrum. Optionally, this procedure may be monitored or performed laparoscopically, at least in part.

The distender 50A includes staples 62, drive member 54' and staple forming means (not shown). The staple forming means may comprise an anvil as described, for example, in U.S. Pat. Nos. 3,873,016; 4,202,480; 4,317,535 and 4,527, 725 (the entire contents of which are herein incorporated by reference). To operate the distender 50A, the vagina 26 is placed between the implantable article 10' and the end portion 54A. The drive member 54' may be moved in the direction of the arrow in FIG. 5. The drive member 54' drives the staples 62 against anvils, through vaginal tissue 26, through ends 14' and 16' of implantable member 10' and forms the staples into the "B" shapes shown in FIG. 5.

The kit 90 may be in the form of a plurality of prepackaged articles. Alternatively, the elements of the kit may be provided in a single package.

The elements of the kit 90 are preferably supplied in a sterile package. The elements may be sterilized by any suitable sterilization means, including steam sterilization, ethylene oxide sterilization, plasma sterilization, hydrogen peroxide vapor sterilization, peracetic acid sterilization, IR sterilization or the like.

While implantable article 10 is preferably Y-shaped for addressing vaginal prolapse during a sacral colpopexy in females, other shapes are also contemplated. Depending on the treatment addressed (e.g. to address a rectocele, enterocele or prolapse) the implantable article may be any of a wide variety of shapes. FIG. 5 illustrates another embodiment of implantable article according to the present invention. The implantable article shown in that Figure includes a base portion 18A, and two tissue engagement portions 14A and 16A. Tissue engagement portion 14A has a length less than that of tissue engagement portion 16A.

Figure 6:
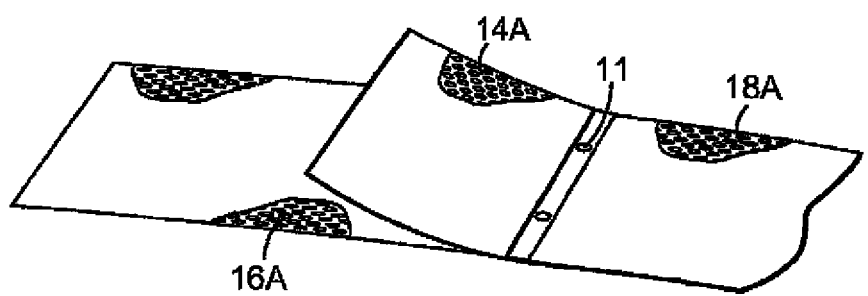
FIG. 6 is a perspective view of another embodiment of implantable article according to the present invention.

The implantable article shown in FIG. 6 includes a separation force distribution means in the form of an acetal clip 11. The acetal clip may be attached to the implantable article before or during surgery. The acetal clip may be used to adjust the tension of the implantable article. In one embodiment, the acetal clip 11 may be insert molded around the sling material providing an attachment point for sutures to be attached.

While the base portion (e.g. 18A) is illustrated as a flat strip, it is also contemplated that the base portion could comprise one or more (preferably two) sutures (e.g. 43 in FIG. 11) extending from the bone screws (e.g. 44 in FIG. 3) to one or more sutures holes in the acetal clip 11. The sutures 43 could be cut and tied to adjust the tension of the implantable article. It is believed that the tension of an implantable article with sutures 43 serving as a base portion may be more readily adjustable postoperatively than an implant with a base portion strip (e.g. 18A).

Figure 7:
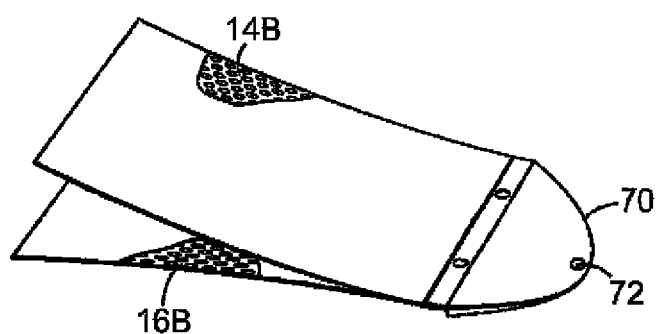
FIG. 7 is perspective view of another embodiment of implantable article according to the present invention.

FIG. 7 illustrates another embodiment of implantable article according to the present invention. The implantable article includes a base portion 70 with sutures hole 72 and tissue engagement portions 14B and 16B.

Figure 13:
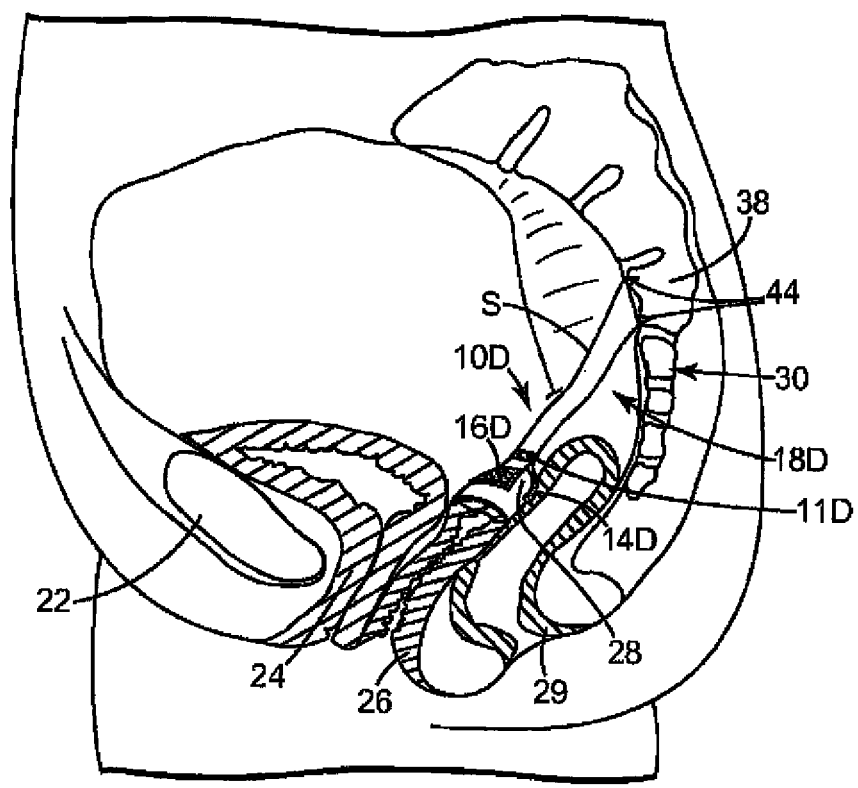
FIG. 13 is a schematic side view of a patient after an alternative embodiment of implantable article has been inserted.
Figure 14:
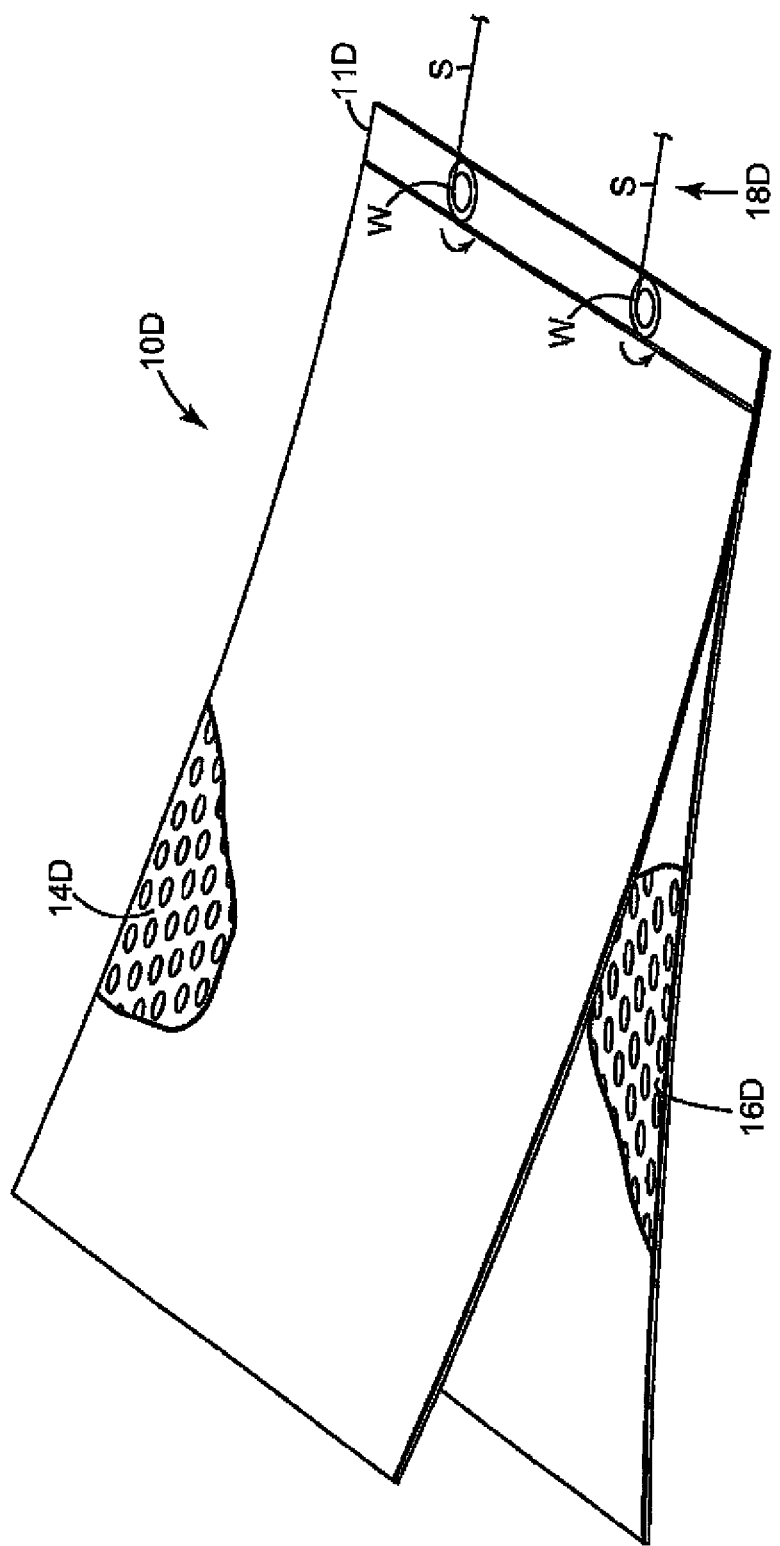
FIG. 14 is a schematic view of the implantable article of FIG. 13.

The implantable articles of the present invention may also include other optional features. FIGS. 13 and 14 illustrate another embodiment of implantable article 10D. The implantable article 10D includes tissue engagement portions 14D and 16D. Instead of a fabric base portion, the article 10D includes at least one (and preferably two) sutures S which form a bridge to anatomical structure such as bone, ligament or soft tissue.

FIG. 13 illustrates the article 10D implanted in the body. The vagina 26, sacrum 30, urethra 24, pelvic bone 22, vaginal cuff 28 and rectum 29 are again shown schematically and should not be interpreted as being shown to scale or for anatomical precision. Preferably, the sutures bridge to bone screws 44 implanted in the sacrum 30 (preferably sacral segment three 38). Alternatively, the sutures may anchor to ligament or soft tissue.

FIG. 14 illustrates a preferred embodiment of implantable article 10D. The implantable article includes a clip 11D. The implantable article 10D preferably includes means for taking up and/or providing suture S length to adjust the tension of the article 10D. The means may afford adjustment of the tension of implantable article during the surgical procedure or after the surgical procedure. The article 10D may also include a means for preventing excessive tension from being applied to the suture of a bone anchor.

As shown in FIG. 14, the means may comprise one or more rotatable wheels W. The wheels W may be rotated in the direction of the arrows to tighten the tension in the sutures S (and correspondingly, the tension in implantable article 10D). Rotation of the wheels W in the opposite direction loosens tension. The implantable article may also be constructed so that the tension of the article may only be tightened. Alternatively, the implantable article may be constructed so that the tension of the article may only be loosened. The wheels W preferably include an indexing mechanism (not shown) for holding the wheel in a particular position.

Figure 15:
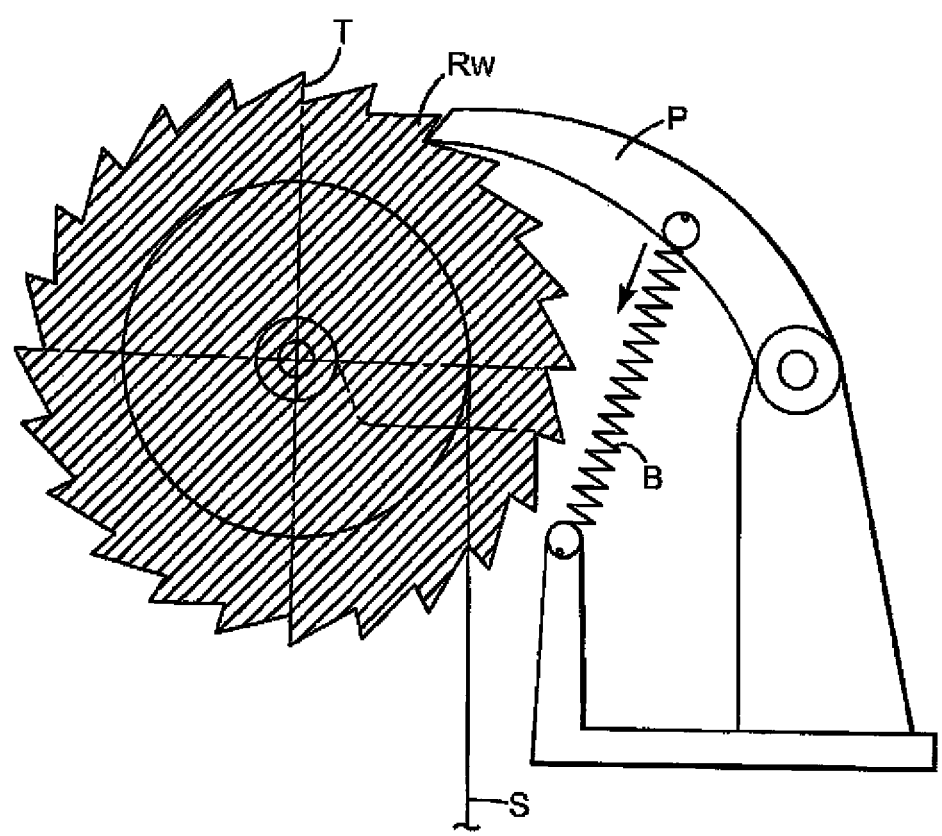
FIG. 15 is a schematic view of elements of an implantable article according to a preferred embodiment of the present invention.

FIG. 15 illustrates a preferred embodiment. For example, the article 10D may include a ratchet wheel RW having a plurality of ratchet teeth T, pawl P and biasing spring B. The pawl P would allow rotation of the wheel RW in one direction (e.g. to tighten the implantable article 10D), but not in the other direction. The pawl also retains the wheel in a place until the wheel RW is rotated. An incision in the vagina may be made to gain access to the wheel RW to rotate it with a surgical tool similar to a screwdriver. A slot on the wheel RW may be adapted to engage the screwdriver to afford rotation of the wheel RW.

In cases of vaginal shortening due to scaring or previous surgeries, the ability to tension the device post operatively may afford gradual restoration of vaginal length. If the ratchet wheel is constructed from a radioopaque material and from a material (e.g. metal) that may be moved by virtue of a remote force (e.g. a magnetic field), then the article 10D may afford the ability to adjust the tension without a subsequent surgical incision. After the surgical procedure, a surgical device capable of delivering a remote force (e.g. one similar in shape to the vaginal distender) may be inserted in the vagina and used to rotate the ratchet wheel W without an incision. The actual location of the ratchet wheel may be monitored by virtue of the radioopaque nature of the wheel.

In another embodiment, a remotely actuatable mini-motor may be incorporated in the implantable article to afford post operative adjustment of the implant. For example, the motor could comprise a miniature brushless motor generally available from Micro Mo Electronics Inc., of Clearwater, Fla.

Other alternatives for attachment of sutures include the folding of the implantable article over a small diameter acetal rod and silicone insert molding the rod into the fold of the implantable article. Alternatives to insert molding include a folding acetal clip that clips on to a preferred sling material in such a manner as to provide places for attachment of sutures. The acetal clip may have holes for sutures or provide a yoke for suture attachment. This affords a convenient and easy method of making a Y-shaped implantable article without sewing or suturing. It also creates a secure place for suture fixation and possible future adjustment. Even without an adjustment mechanism incorporated into the attachment point, future tensioning or loosening is facilitated as implantable fabric does not extend a great distance (e.g. to the sacrum for a sacral colpopexy) and this allows for replacement of fixation sutures without removal of a large amount of ingrown tissue.

In another embodiment of implantable article according to the present invention, the adjustment mechanism may be incorporated to tension or loosen the implantable article between the vaginal cuff and the sacrum in the immediate postoperative period. Access to the adjustment means may be achieved through an abdominal incision, laparoscopically, or preferably via a minimally invasive vaginal incision. A remotely actuatable mechanism (e.g. a magnet) may also be employed. This could be accomplished with a ratchet/pawl mechanism similar to that shown in FIG. 15.

In another embodiment of the invention, one or more substances may be associated with the implantable article 10 by, for example, a coating process. The substances may be used to enhance treatment effects, indicate proper orientation, enhance visibility, encourage tissue ingrowth, resist infection or other effects. For example, the implantable article 10 may be dyed a contrasting color (e.g. blue) relative to its physiological environment. The contrasting color of the implantable article 10 provides the surgeon with a visual indicator that can be used to confirm proper orientation. In addition to coating substances, other components including, without limitation, tags, labels or indicia may also be used to indicate proper sling orientation or enhance visibility/identification.

EXAMPLES

A variety of materials and construction techniques may be used in conjunction with the present invention. As an example, not intended to be limiting, the material may comprise any of the materials described in U.S. Provisional Patent Application No. 60/230,647, filed Sep. 7, 2000 (the entire contents of which are herein incorporated by reference).

Example 1

Material and Method

The implantable article 10 is preferably constructed from a base or backing material, e.g. a tightly woven polyester mesh having a plurality of pores. The polyester mesh is ultimately coated with a silicone dispersion. The base material may be a Rashel knit mesh made from 150 dernier polyester yarn. In an uncoated state, the thickness may be between about 0.01 inches and about 0.04 inches, preferably about 0.020 inches (0.508 mm). The mesh has a hole size of approximately 1/32" (25.4 mm) and a weight of approximately 4.7 oz/yard (133.25 grams/0.914 m) constructed from polyester or polypropylene. Preferably, the pore density is between 50 and 400 pores/square inch, more preferably about 240 pores per square inch. After coating, the size of the holes or pores is preferably in the range of about 0.040 inches (1.016 mm) to about 0.055 inches (1.397 mm).

The polyester material is coated with a silicone material (e.g. NuSil MED 6820, available from NuSil of Carpinteria, Calif.) by a dip coating process. The silicone dispersion results from mixing equal parts (e.g. 100 g each) of Medium 6820 with about 5 parts (e.g. 500 g) solvent such as Xylene. Stirring on a stir plate in a fume hood can mix the dispersion. Mixing should be performed for a minimum of 20 minutes with the container covered to Minimize evaporation.

A container or reservoir (e.g. pan) is filled with the silicone dispersion for immersion of the mesh material. The pan is covered to resist evaporation.

The mesh is placed in the dispersion mix and is held flat by use of, for example, 8 inch (15.24 cm) embroidery hoops. When using embroidery hoops, the mesh material should be pulled through the edges of the hoop until the mesh material is taut, flat and constrained along most if not all of the peripheral edge of the mesh material. Care is taken not to inordinately stretch the material as this may result in distortion of the holes of the mesh material or in uneven coating of the mesh material. The mesh material should be trimmed to be sized closely to the dimensions of the hoop so as to minimize overlap. The hoop containing the mesh material is placed into the reservoir containing the silicone dispersion for about 15 seconds, or more and then removed.

In another embodiment of method, the material can be held in tension at opposite ends of the sheet prior to applying the coating. In yet another embodiment, a roll of the mesh may be continuous fed into a reservoir and then further processed (e.g. heated, and/or air blown as described below) in web form.

Excess silicone dispersion is removed by allowing the silicone to drip off of the mesh material as the hoop is placed flat over the pan for about 1-5 minutes.

The coatings within the holes of the material are cleared. This may be accomplished by using a foot controlled air nozzle with an air setting of approximately 55-psi and 600 pulses per minute. Using the air nozzle, the coated mesh material can be continuously sprayed to free the openings until there are minimal or no holes filled with silicone dispersion. Alternatively, the spraying can be performed intermittently. The coated material is rested, air-sprayed side up, for approximately 5-15 minutes.

The steps above (starting with filling a reservoir) may be repeated with the exception that the second side of the mesh material is now air sprayed to provide a uniform distribution of the silicone coating over all surfaces of the material.

The spraying ensures that the holes or pores of the mesh are not filled or closed with silicone. Preferably, the implantable article of the present invention includes open pores or holes to encourage tissue ingrowth and to resist infection.

Preferably, the above steps are repeated until the material has at least two coatings of silicone dispersion. More preferably, the process is repeated six times.

The silicone coating is then preferably heated to set the silicone dispersion. This may be accomplished by hanging the hoops holding the material in an oven that is set at 160 degrees Celsius (+/-10 degrees) for about 20 minutes. The material is then removed from the oven and allowed to cool. The material is then cut from the hoop. Optionally, an anti-microbial substance or medicament may be impregnated into the silicone elastomer during this process or during a subsequent process.

Preferably, the material is configured in a long narrow elongated piece. The width is approximately the same width as the implantable article. The edges of the material along the length of the material are coated with silicone by the above process. When an elongated material is used, all that is required to obtain a sling suitable for use in a patient is to cut the elongated material through its width at the desired length of the implantable article. This yields an implantable article that has the edges along the longitudinal side of the material completely coated with silicone (with the integrity of the coating along the longitudinal side intact). Optionally, a material cut along an end may be redipped in silicone to coat a cut edge.

The thickness of the final coated material was between about 0.024 and about 0.036 inches.

Alternatively, the material may be supplied according to the teachings of Cabak et al., U.S. Patent No. 60/230,647, filed on Aug. 24, 2001 (on the even date of the present application) (the entire contents of which are herein incorporated by reference).

Example 2 Construction

Figure 8:
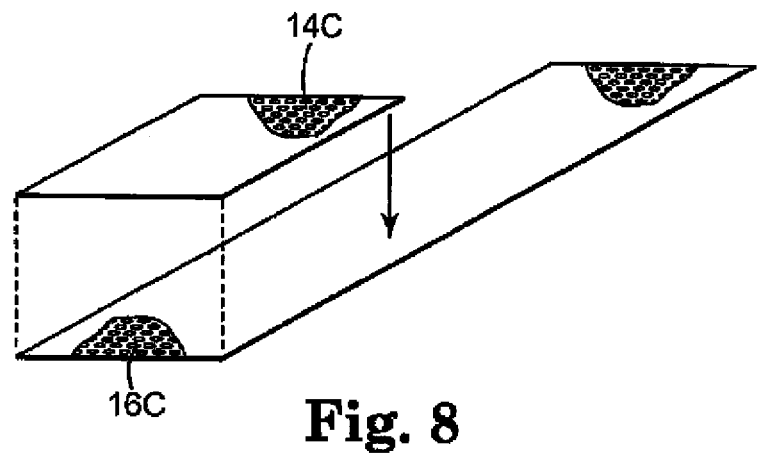
FIG. 8 is a perspective view illustrating a step in a method of making or preassembling the implantable article of FIG. 1.

Referring to FIG. 8, the silicone coated material of Example 1 was cut into two rectangular components each having a width of about 38 to about 42 mm. The larger component 16C had a length of about 147.3 to about 152.4 mm. The smaller component 14C had a length between about 43 and about 45 mm.

The larger component 16C was placed on a flat fixture and the smaller component 14C was placed on top of it. The edges are even and substantially parallel as shown in FIG. 8.

Figure 9:
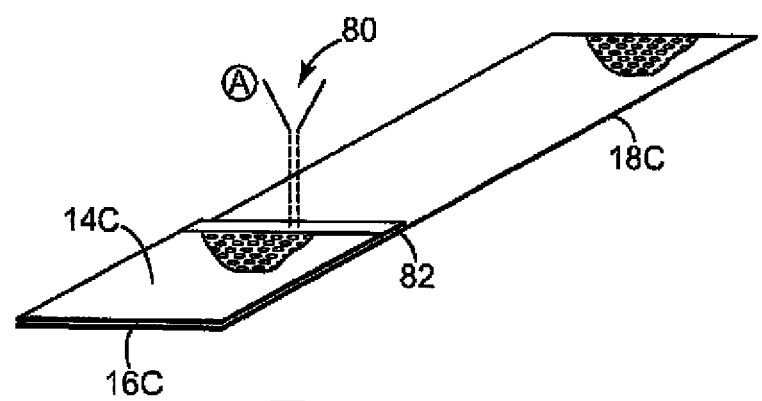
FIG. 9 is a perspective view illustrating a step in a method of making or preassembling the implantable article of FIG. 1.

A dispenser having two separate reservoirs, a static mixer, and nozzle 80 is positioned at the edge of the smaller component 14C as shown in FIG. 9. The components of the liquid silicone elastomer (e.g. MED-4840 LSR elastomer, generally available from NuSil) are loaded into the reservoirs.

The elastomer is placed at the edge of the short portion 14C so that it flows through the pores and provides a layer of elastomer at the top and bottom of the bond. Preferably, at least two full rows of pores are completely filled with elastomer.

The assembly may be placed in an oven at 110 degrees Celsius for 6 minutes minimum. The finished assembly exhibited excellent resistant to pull apart loading (19.1 lbs.) and cyclical load wear.

Example 3

Figure 10:
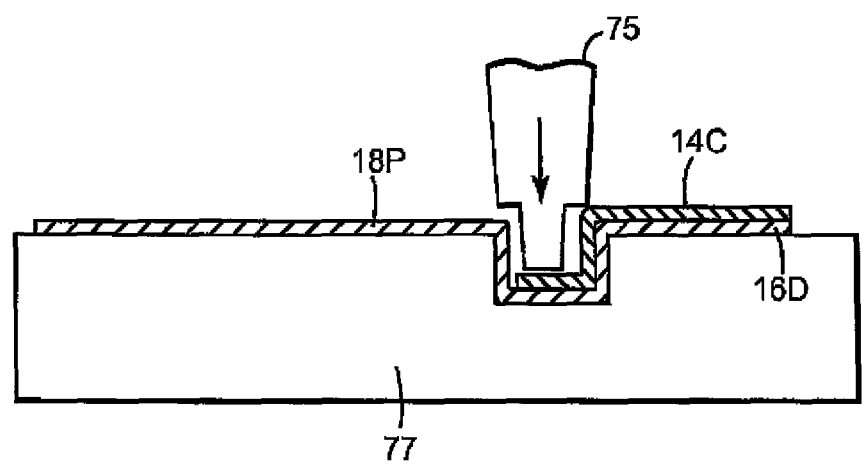
FIG. 10 is a schematic view of another method of making an implantable article according to another aspect of the present invention.

FIG. 10 illustrates an example similar to that of Example 2, except that a recessed fixture 77 is used. The nozzle 75 may be used to press against the edge of the short portion 14C of the implant. This process may be manual or automated in whole or in part.

This example comprises a method of making an implantable surgical article comprising the steps of (1) providing a thin, first strip with first and second ends, major surfaces, and a length between the first and second ends; (2) providing a thin, second at with first and second ends, major surfaces, and a length between the first and second ends; the length of the second strip being less than that of the first strip; (3) placing a major surface of the first strip against a major surface of the second strip; and (4) bonding the first strip to the second strip.

Preferably, the step of bonding the first strip to the second strip includes the step of bonding the first strip to the second strip with a silicone elastomer.

Also preferably, the process includes the step of providing a fixture with a recessed portion. The step of placing a major surface of the first strip against a major surface of the second strip preferably includes the step of placing at least a portion of the first and second strips in the recessed portion of the fixture; and the step of bonding includes the step of bonding the portion of the first strip within the recessed portion to the portion of the second strip within the recessed portion.

Surgical Procedures

Many surgical methods are contemplated herein. Although the methods of use as disclosed herein generally relate to female disorders and treatments/procedures, male disorders and treatments/procedures are also included within the scope of the present invention.

Abdominal Incision/Bone Anchors

The present invention may be utilized to address vaginal vault prolapse. The patient is placed in the lithotomy position using padded lower thigh and calf support, and drapes are applied preferably using both leggings and laparotomy sheet. A kit having bone anchor screws and other elements described above may be used to perform a sacral colpopexy.

The anterior abdomen, vagina and bowel are thoroughly prepped and a standard Foley catheter is inserted into the urinary bladder. The sterile manipulating vaginal distender (e.g. see FIG. 4) is inserted.

The abdomen is opened via a midline or Pfannenstiel incision and a self-retaining ring retractor is positioned. The sigmoid colon is held to the patient's left. A midline incision is made in the posterior peritoneum overlying the midline of the sacrum after identification of the right ureter. This incision is made with electrocautery and carried through the retroperitoneal fat tissue to the periosteum of the sacrum.

The implantable article of the present invention is secured. It is preferably preassembled, in the shape shown in FIG. 1 and measuring 17 cm in overall length, 4 cm in width (with the minor leg portions having a length of about 8 cm).

After the posterior parietal peritoneum overlaying the sacral promontory is opened (e.g. longitudinally), the periosteum of the sacrum is selected for placement of bone anchor screws with attached sutures. Preferably sacral segment three ($S_3$) is selected. Optionally, other sacral segments may be selected according to a variety of factors such as surgeon experience level, the particular anatomy structure of the patient, and tissue condition.

Caution is exercised to avoid disruption of the presacral veins (e.g. the middle sacral vein traversing over the promontory) and any proximate vessels or nerves. The bone anchor screws may be placed using a powered inserter such as the Straight-In Inserter, generally available from American Medical Systems, Inc. of Minnetonka Minn. The screws are initially loaded into the inserter device. The tip of the loaded screw is placed perpendicular to the bone. The surgeon presses the inserter's operating button until the screw is completely inserted. The operating button is released and the inserter is removed. Preferably, the screws are placed 1-1.5 cm apart vertically in the midline or horizontally on either side of the sacral segment, depending on the pattern and location of the adjacent veins, nerves and vessels. The sutures from the bone anchors may then be tagged and attention turns to preparation of the vaginal apex.

With one hand manipulating the vaginal distender, the vaginal apex is freed of attached bladder using sharp and blunt dissection for a distance of about 3-4 cm. It is rarely necessary to dissect tissue from the posterior vaginal apex unless bowel is adherent in an enterocele.

The anterior and posterior segments of the implantable article are secured to the vaginal apex using about 6 to 10 uninterrupted nonabsorbable sutures (e.g. spaced 1.5 cm apart), fore and aft, driving the suture needle against the distender to preferably produce a full-thickness graft of the vaginal apex. Once the implantable article is secured to the vaginal apex, the vaginal distender can be removed and discarded. Alternatively, a tissue adhesive may be used in conjunction with the suturing or in the place of the suturing.

The sutures of the bone anchors are used to tie the base of the implantable article to the bone anchors. Preferably, tension should be avoided while fixing the base of the implantable article to the bone anchors. For example, about 1 cm slack may be provided. The implantable article preferably provides a hammock of support, so that any increase in intra-abdominal pressure will be transmitted to the implantable article, flattening the vaginal apex against the sacrum. Redundant portions of the implantable article may be trimmed and reperitonealization performed with interrupted sutures placed so as to completely cover the implantable article.

Optionally, retropubic urethropexy may be performed (unless previously performed), as elevation of the vaginal apex tends to flatten the posterior urethrovesical angle. These steps may help avoid genuine stress urinary incontinence.

After thorough irrigation of the operative site, the abdomen may be closed.

Bone Sutures

This procedure is similar to the abdominal incision process described above except that the kit need not include bone screws or a surgical device for inserting bone screws. Instead, after the anterior surface of the sacral promontory is visualized, two or three sutures (e.g. polyester or polypropylene sutures suitable for use in bone) may be placed in the periosteum over the sacral promontory using, for example a M0-6 or M-07 needle.

The sacral promontory sutures are then used to secure the implantable article to the promontory. Tension in the implantable article is avoided and any excessive length of the implantable article is trimmed.

Laparoscopic Technique

The abdomen is insufflated using a conventional pneumoneedle. A plurality of cannula ports are opened with safety trocars at locations apt to avoid sensitive structures such as the inferior epigastric artery, the external iliac artery, the superficial epigastric artery, and the superficial circumflex iliac artery. Five and ten millimeter ports are preferred.

After the ports are placed, the peritoneum is dissected off the vaginal apex to delineate the rectovaginal fascia. Anterior dissection is performed. The vaginal distender is used to identify the vaginal apex.

The peritoneum overlying the sacral promontory is incised longitudinally and extended to the cul-de-sac. A laparoscopic dissector or hydrodissection may be used to expose the periosteum of the sacral promontory.

The implantable material is introduced through a port (preferably a 10/12 mm port). The implantable article may be sutured (e.g. with no. 0 non-absorbable sutures) to the anterior and posterior portions of the vaginal apex (3 rows each) with a laparoscopic suturing device. The stitches are placed through the entire thickness of the vaginal wall.

The implantable article is then attached to the sacrum or the ligament of the sacrum or the anterior sacral fascia (longitudinal ligament). Two no. 0 or 2-0 non-absorbable sutures may be used for this purpose. Alternatively, titanium tacks, bone anchors, bone screws or hernia staples may be used to attach the base of the implantable article. Any excess portion of the implantable article may be trimmed.

A laparoscopic compatible surgical device may be used to place the bone anchors (e.g. screws). For example, a manual screw driver or a powered screw driver that is sized and shaped to fit in the cannula of a trocar may be utilized for this purpose.

The peritoneum is reapproximated over the implantable article (e.g. with no. 2-0 polyglactine sutures). The ports are removed and the incisions closed.

Transvaginal Approach

A transvaginal suspension is described in Nichols D H: *Sacrospinous Fixation For Massive Eversion of the Vagina*, AM J. Obstet Gynecol 1982; 142:901-904 (the entire contents of which are herein incorporated by reference). Essentially, a vaginal incision is made and the vaginal vault is suspended from the sacrospinal ligament. The Nichols technique may be modified by using an implantable article according to the present invention. Preferably, a preassembled, V-shaped implantable article as described above may be used.

No Implant

As discussed above, the distender 50A of FIG. 5 may be utilized to tack the vagina directly to tissue or bone (e.g. the sacrum).

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. A method of treating a pelvic floor disorder comprising:
   providing an implant comprising two tissue engagement portions and a base portion,
   creating an incision,
   attaching the two tissue engagement portions to a vaginal cuff, and
   attaching the base portion to an anterior longitudinal ligament.

2. The method of claim 1 wherein one of the tissue engagement portions is attached to an anterior vaginal cuff and one of the tissue engagement portions is attached to a posterior vaginal cuff.

3. The method of claim 1 wherein each engagement portion is attached to the vaginal cuff via attachment means selected from the group consisting of adhesives, bonding agents, mechanical fastener, and suture.

4. The method of claim 3 wherein the attachment means is a suture, and wherein a tension of the implant can be adjusted via the suture.

5. The method of claim 1 wherein creating the incision includes creating a vaginal incision.

6. The method of claim 1 wherein creating the incision includes creating an abdominal incision.

7. The method of claim 1 wherein the method of treating a pelvic floor disorder is a laparoscopic procedure.

8. The method of claim 1 wherein the method further comprises attaching a posterior end of one of the two tissue engagement portions to a posterior end of the other of the two tissue engagement portions.

9. The method of claim 8 wherein the method further comprises attaching an anterior end of the base portion to the posterior ends of the two tissue engagement portions.

10. The method of claim 1 wherein the base portion is attached to the anterior longitudinal ligament via attachment means selected from the group consisting of adhesives, bonding agents, mechanical fastener, and suture.

11. The method of claim 1 wherein the pelvic floor disorder is selected from vaginal vault prolapse, enterocele, rectocele, and cystocele.

12. The method of claim 1 wherein the method of treating a pelvic floor disorder is a sacral colpopexy procedure.

* * * * *